United States Patent [19]

Steiner et al.

[11] Patent Number: 5,306,600
[45] Date of Patent: Apr. 26, 1994

[54] OXYGEN-CONTAINING TITANOCENES, AND THE USE THEREOF

[75] Inventors: Eginhard Steiner, Füllinsdorf; Harry Beyeler, Basel; Martin Riediker, Rorbas; Vincent Desobry, Marly; Kurt Dietliker, Fribourg; Rinaldo Hüsler, Wünnewil, all of Switzerland

[73] Assignee: Ciba-Geigy Corporation, Ardsley, N.Y.

[21] Appl. No.: 975,042

[22] Filed: Nov. 12, 1992

Related U.S. Application Data

[62] Division of Ser. No. 527,988, May 23, 1990, Pat. No. 5,192,642.

[30] Foreign Application Priority Data

Jun. 1, 1989 [CH] Switzerland ............... 2074/89

[51] Int. Cl.$^5$ .............. G03F 7/029; C07F 17/00
[52] U.S. Cl. .................... 430/281; 430/947; 430/923; 522/26; 522/66; 502/152; 502/156; 502/155; 556/53; 556/11; 544/4; 544/64; 544/225; 546/2; 546/4; 546/11; 546/12; 549/3; 549/206
[58] Field of Search ........ 430/281, 947, 923; 522/29, 66; 502/152, 156, 155; 556/53, 11; 544/4, 64, 225; 546/2, 4, 11, 12; 549/3, 206

[56] References Cited

U.S. PATENT DOCUMENTS

| | | | |
|---|---|---|---|
| 4,590,287 | 5/1986 | Riediker et al. | 556/53 |
| 4,713,401 | 12/1987 | Riediker et al. | 522/65 |
| 4,857,654 | 8/1989 | Riediker et al. | 430/281 |
| 4,963,470 | 10/1990 | Klingart et al. | 430/281 |
| 5,008,302 | 4/1991 | Hüsker et al. | 430/920 |
| 5,026,625 | 6/1991 | Riediker et al. | 430/281 |
| 5,055,372 | 10/1991 | Shanklin et al. | 430/138 |
| 5,192,642 | 3/1993 | Steiner et al. | 430/281 |

FOREIGN PATENT DOCUMENTS

| | | |
|---|---|---|
| 0256981 | 2/1988 | European Pat. Off. |
| 0318893 | 6/1989 | European Pat. Off. |
| 0318894 | 6/1989 | European Pat. Off. |

OTHER PUBLICATIONS

M. A. Chaudhari et al., J. Organomet. Chem., 2, 206, (1964).
C. Tamborski et al., J. Organomet. Chem., 4, 445 (1965).

Primary Examiner—Marion E. McCamish
Assistant Examiner—Mark A. Chapman
Attorney, Agent, or Firm—William A. Teoli, Jr.

[57] ABSTRACT

Titanocenes of the formula I

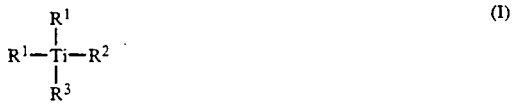

in which $R^1$ are cyclopentadienyl$^\ominus$ groups and $R^2$ and $R^3$ are aromatic radicals which are substituted in both ortho-positions by fluorine and, in addition, are substituted by an acyloxy group are suitable as photoinitiators for the photopolymerization of ethylenically unsaturated compounds.

4 Claims, No Drawings

OXYGEN-CONTAINING TITANOCENES, AND THE USE THEREOF

This is a divisional of Ser. No. 07/527,988, filed May 23, 1990, now U.S. Pat. No. 5,192,642.

The present invention relates to titanocenes containing fluorine-containing aromatic radicals carrying esterified oxygen functions, to a process for the preparation thereof and to the use thereof as photoinitiators for the polymerization of ethylenically unsaturated compounds.

U.S. Pat. No. 4,590,287 discloses that titanocenes containing fluoroaryl ligands are excellent photoinitiators. The fluoroaryl ligands of these titanocenes may be substituted, for example, by hydroxyl, alkoxy, carboxyl, alkoxycarbonyl or aminocarbonyl. U.S. Pat. No. 4,857,654 discloses titanocenes having polyoxaalkylene chains on the fluoroaryl ligands. EP-A-256,981 describes titanocenes containing silylated cyclopentadienyl radicals. EP-A-318,894 discloses titanocenes having pyrrole substituents on the fluoroaryl ligands, EP-A-318,893 describes titanocenes having nitrogen-containing ligands on the fluoroaryl radical and U.S. Pat. No. 4,713,401 discloses titanocenes which have $CF_3$ substituents in place of fluorine atoms on the aryl ligands. Substitutions by acyloxy groups, carbamoyloxy groups, sulfonyloxy groups or siloxy groups have hitherto not been disclosed. However, it has been shown that titanocenes substituted in this manner are likewise excellent photoinitiators and are distinguished by improved solubility.

The invention relates to titanocenes of the formula I

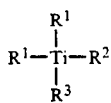 (I)

in which both the $R^1$ radicals, independently of one another, are cyclopentadienyl$^\ominus$, indenyl$^\ominus$ or 4,5,6,7-tetrahydroindenyl$^\ominus$, each of which is unsubstituted, monosubstituted or polysubstituted by $C_1$-$C_{18}$alkyl, $C_1$-$C_{18}$alkoxy, $C_2$-$C_8$alkenyl, $C_5$-$C_8$cycloalkyl, $C_6$-$C_{10}$aryl, $C_7$-$C_{16}$aralkyl, —Si(R$^4$)$_3$, —Ge(R$^4$)$_3$, cyano or halogen, and $R^4$ is $C_1$-$C_{12}$alkyl, $C_5$-$C_8$cycloalkyl, $C_6$-$C_{10}$aryl or $C_7$-$C_{16}$aralkyl, $R^2$ is a 6-membered carbocyclic or 5- or 6-membered heterocyclic aromatic ring which is substituted by fluorine atoms at least in the two ortho-positions to the titanium-carbon bond, and in which the aromatic ring may contain further substituents, and $R^3$, independently, is as defined for $R^2$, $R^2$ and $R^3$ in the titanocenes being substituted by a radical of the formula II

—O—Y—R$^5$ (II)

in which Y is a —CO—, —CS—, —CO—O—, —SO$_2$—, —Si(R$^4$)$_2$, —CO—NR$^6$—, —CS—NR$^6$— or —SO$_2$—NR$^6$— group, R$^5$ is linear or branched $C_1$-$C_{20}$alkyl, $C_2$-$C_{20}$alkenyl, $C_3$-$C_8$cycloalkyl, $C_4$-$C_{20}$cycloalkylalkyl, $C_4$-$C_{20}$alkylcycloalkyl, $C_5$-$C_{20}$alkylcycloalkylalkyl, $C_6$-$C_{20}$cycloalkenylalkyl, $C_7$-$C_{20}$bicycloalkyl, $C_6$-$C_{14}$aryl, $C_7$-$C_{12}$aralkyl, $C_7$-$C_{20}$alkyl or $C_8$-$C_{20}$alkylaralkyl, these radicals being unsubstituted or substituted by $C_1$-$C_{18}$alkoxy, $C_1$-$C_{12}$alkylthio, $C_1$-$C_{18}$alkylsulfonyl, $C_6$-$C_{10}$arylsulfonyl, $C_7$-$C_{20}$alkylarylsulfonyl, —COOH, —CN, —COOR$^4$, —CO—($C_1$-$C_{20}$alkyl) or halogen, $R^6$ is hydrogen or has one of the meanings mentioned for $R^5$, or $R^5$ and $R^6$ together are $C_3$-$C_7$alkylene, which may be interrupted by —O—, —S— or —N(R$^7$)—, in which $R^7$ is hydrogen, $C_1$-$C_{12}$alkyl, $C_3$-$C_{12}$alkenyl, $C_7$-$C_{12}$aralkyl or $C_2$-$C_{20}$alkanoyl.

The $R^1$ groups are preferably identical radicals. Suitable substituents for $R^1$ are: linear or branched alkyl or alkoxy having 1 to 18, particularly 1 to 12 and in particular 1 to 6, C atoms, and alkenyl having 2 to 18, particularly 2 to 12, and in particular 2 to 6, C atoms, for example methyl, ethyl, propyl, isopropyl, n-butyl, tert.-butyl, pentyl, hexyl, octyl, decyl, dodecyl, tetradecyl, hexadecyl, octadecyl and corresponding alkenyl and alkoxy groups; cycloalkyl having 5 to 8 ring carbon atoms, for example cyclopentyl, cyclohexyl, cycloheptyl, methylcyclopentyl and methylcyclohexyl; aryl having 6 to 10 C atoms and aralkyl having 7 to 16 C atoms, for example phenyl, naphthyl, benzyl and phenylethyl; cyano and halogen, particularly F, Cl and Br, —Si(R$^4$)$_3$ or —Ge(R$^4$)$_3$, in which R$^4$ is preferably $C_1$-$C_8$alkyl, cyclohexyl, phenyl or benzyl. Examples of alkyl R$^4$ are methyl, ethyl, n- and i-propyl, n-, i- and t-butyl, pentyl, hexyl, heptyl and octyl.

The radicals R$^1$ may contain up to 5, but particularly up to 3 substituents. Both R$^1$ groups are preferably cyclopentadienyl$^\ominus$ or methylcyclopentadienyl$^\ominus$ radicals, in particular cyclopentadienyl$^\ominus$ radicals.

R$^2$ as a 6-membered carbocyclic, aromatic ring which is substituted by at least 2 fluorine atoms may be, for example, fluorine-substituted indenyl, indanyl, fluorenyl, naphthyl or phenyl which are substituted by a radical of the formula II. R$^2$ as a 5- or 6-membered heterocyclic, aromatic ring substituted by at least 2 fluorine atoms may contain 1 or 2 hetero atoms and may be, for example, fluorine-substituted furyl, thienyl, pyrryl, pyridyl, pyrimidyl or pyridazyl which are substituted by a radical of the formula II. R$^2$ is preferably a carbocyclic ring.

R$^3$ is preferably as defined for R$^2$.

R$^2$ and R$^3$ are preferably 2,6-difluorophen-1-yl to which a radical of the formula II is bonded, and which may contain a further 1 or 2 identical or different substituents.

R$^2$ and R$^3$ are preferably a group of the formula III

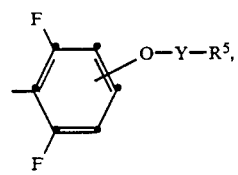 III in which Y and R$^5$ are as defined above. In the formula III, the —O—Y—R$^5$ group is preferably in the ortho-position to a fluorine atom. In this case, R$^2$ is a group of the formula IIIa

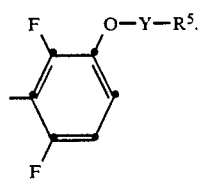 IIIa $R^2$ and $R^3$ may preferably also be a group of the formula IV

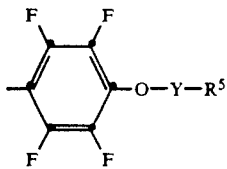

in which Y and $R^5$ are as defined above.

$R^5$ may be linear or branched $C_1$-$C_{20}$alkyl, preferably $C_1$-$C_{12}$alkyl and particularly $C_1$-$C_8$alkyl. Examples are methyl, ethyl and the isomers of propyl, butyl, pentyl, hexyl, heptyl, octyl, nonyl, decyl, undecyl, dodecyl, tetradecyl, hexadecyl and octadecyl. $R^5$ may be $C_3$-$C_8$cycloalkyl, preferably $C_5$-$C_8$cycloalkyl and particularly $C_5$- or $C_6$cycloalkyl, for example cyclopropyl, cyclobutyl, cyclopentyl, cyclohexyl, cycloheptyl and cyclooctyl. $R^5$ may be $C_4$-$C_{20}$cycloalkylalkyl or -alkylcycloalkyl, preferably $C_6$-$C_{15}$cycloalkylalkyl or -alkylcycloalkyl, the cycloalkyl preferably being cyclopentyl or cyclohexyl. Examples are cyclopentyl- or cyclohexylmethyl, cyclopentyl- or cyclohexylethyl, cyclopentyl- or cyclohexylpropyl, cyclopentyl- or cyclohexylbutyl, methyl-, dimethyl-, ethyl-, n-propyl-, i-propyl-, n-butyl-, i-butyl- or t-butylcyclopentyl or -cyclohexyl. $R^5$ may be $C_5$-$C_{20}$alkylcycloalkylalkyl, preferably $C_7$-$C_{16}$alkylcycloalkylalkyl, for example (methylcyclopentyl)methyl or -ethyl or (methylcyclohexyl)methyl or -ethyl.

$R^5$ may also be $C_6$-$C_{14}$aryl, preferably $C_6$-$C_{10}$aryl, for example naphthyl and particularly phenyl. $R^5$ may also be $C_7$-$C_{20}$aralkyl or -alkaryl, preferably $C_7$-$C_{16}$aralkyl or -alkaryl. The aryl here is preferably a phenyl radical. Examples are benzyl, phenylethyl, phenylpropyl, phenylbutyl, methylphenyl, ethylphenyl, propylphenyl and butylphenyl. $R^5$ may also be $C_8$-$C_{20}$alkaralkyl, preferably $C_8$-$C_{16}$alkaralkyl, in which the aryl is preferably phenyl. Examples are methylbenzyl, (methylphenyl)ethyl, (methylphenyl)propyl, (methylphenyl)butyl, ethylbenzyl and propylbenzyl.

These hydrocarbon radicals may be substituted by $C_1$-$C_{18}$alkoxy, in particular $C_1$-$C_{12}$alkoxy or $C_1$-$C_4$alkoxy; by $C_1$-$C_{12}$alkylthio, in particular $C_1$-$C_4$alkylthio; by $C_1$-$C_{18}$alkylsulfonyl, $C_6$-$C_{10}$arylsulfonyl, $C_7$-$C_{20}$alkylarylsulfonyl, —COOH, —CN—COOR$^4$, —CO—(Cl-$C_{20}$alkyl) or by halogen. Examples of such substituted $R^5$ radicals are trichloromethyl, trifluoromethyl, 4-chlorophenyl, 3-bromophenyl, 4-methoxyphenyl, 4-methylthiophenyl, carboxyethyl, carboxyvinyl, carboxyphenyl, cyanomethyl, cyanoethyl or acetylmethyl.

If $R^5$ and $R^6$ together are $C_3$-$C_7$alkylene, which may be interrupted by —O—, —S— or —N($R^7$)—, they form, together with the N atom to which they are bonded, a heterocyclic ring, for example a pyrrolidine, piperidine, methylpiperidine, morpholine, thiomorpholine, piperazine, N-methylpiperazine, N-benzylpiperazine or N-acetylpiperazine ring.

Preferred titanocenes of the formula I are those in which $R^2$ and $R^3$ are a group of the formula III or IV in which Y is —CO—, —CO—O—, —SO$_2$—, —CO—NR$^6$—, —CS—NH— or —SO$_2$NR$^6$—, $R^5$ is $C_1$-$C_{12}$alkyl, cyclohexyl, $C_2$-$C_5$alkenyl, cyclohexylmethyl, $C_7$-$C_{12}$aralkyl, $C_6$-$C_{10}$aryl, phenyl which is substituted by Cl, $C_1$-$C_4$alkyl or $C_1$-$C_4$alkoxy, or is $C_1$-$C_4$haloalkyl or $C_2$-$C_8$alkoxyalkyl, $R^6$ is hydrogen or has one of the meanings given for $R^5$, or $R^5$ and $R^6$ together are $C_4$-$C_5$alkylene or 3-oxapentamethylene.

A further preferred group of compounds are titanocenes of the formula I in which $R^1$ is cyclopentadienyl$^\ominus$ or methylcyclopentadienyl$^\ominus$, and $R^2$ and $R^3$ are a group of the formula III or IV in which either a) Y is —CO— or —SO$_2$— and $R^5$ is $C_1$-$C_{20}$alkyl, $C_2$-$C_8$alkenyl, $C_5$-$C_6$cycloalkyl, $C_6$-$C_{14}$alkylcycloalkyl, $C_6$-$C_{10}$aryl, $C_7$-$C_{18}$alkaryl or chlorophenyl, or b) Y is —CO—O— and $R^5$ is $C_1$-$C_8$alkyl or phenyl, or c) Y is —CO—NR$^6$— and $R^5$ is $C_1$-$C_{12}$cyclohexyl or phenyl and $R^6$ is hydrogen or $C_1$-$C_4$alkyl, or $R^5$ and $R^6$ together are pentamethylene or 3-oxapentamethylene, or d) Y is —Si(R$^4$)$_2$— and $R^4$ is $C_1$-$C_4$alkyl and $R^5$ is $C_1$-$C_8$alkyl or phenyl.

Particularly preferred titanocenes of the formula I are those in which $R^1$ is cyclopentadienyl$^\ominus$ and $R^2$ and $R^3$ are a group of the formula III or IV in which either a) Y is —CO— and $R^5$ is $C_1$-$C_{20}$alkyl or $C_2$-$C_4$alkenyl, or b) Y is —CO—NR$^6$— and $R^5$ is $C_1$-$C_6$alkyl and $R^6$ is hydrogen or $C_1$-$C_4$alkyl, or c) Y is —SO$_2$— and $R^5$ is phenyl or p-tolyl.

Examples of individual compounds of the formula I are:

bis(cyclopentadienyl)bis(2,6-difluoro-3-acetoxyphenyl)titanium, bis(cyclopentadienyl)bis(2,6-difluoro-3-propionyloxyphenyl)titanium, bis(cyclopentadienyl)bis(2,6-difluoro-3-decanoyloxyphenyl)titanium, bis(cyclopentadienyl)bis(2,6-difluoro-3-stearoyloxyphenyl)titanium, bis(cyclopentadienyl)bis(2,6-difluoro-3-methacryloyloxyphenyl)titanium, bis(cyclopentadienyl)bis(2,6-difluoro-3-butyryloxyphenyl)titanium, bis(cyclopentadienyl)bis(2,6-difluoro-3-isobutyryloxyphenyl)titanium, bis(cyclopentadienyl)bis(2,6-difluoro-3-lauroyloxyphenyl)titanium, bis(cyclopentadienyl)bis(2,6-difluoro-3-crotonyloxyphenyl)titanium, bis(cyclopentadienyl)bis(2,6-difluoro-3-oleyloxyphenyl)titanium, bis(cyclopentadienyl)bis(2,6-difluoro-3-benzoyloxyphenyl)titanium, bis(cyclopentadienyl)bis[2,6-difluoro-3-(4-toluyloxy)-phenyl]titanium, bis(cyclopentadienyl)bis[2,6-difluoro-3-thionoacetoxyphenyl]titanium, bis(cyclopentadienyl)bis[2,6-difluoro-3-((isopropylarnino)carbonyloxy)phenyl]titanium, bis(cyclopentadienyl)bis[2,6-difluoro-3-((butylamino)carbonyloxy)phenyl]titanium, bis(cyclopentadienyl)bis[2,6-difluoro-3-((2-methylpropyloxy)carbonyloxy)phenyl]titanium, bis(cyclopentadienyl)bis[2,6-difluoro-3-(4-tolylsulfonyloxy)phenyl]titanium, bis(cyclopentadienyl)bis[2,6-difluoro-3-(phenylsulfonyloxy)phenyl]titanium, bis(cyclopentadienyl)bis[2,6-difluoro-3-(4-dodecylphenylsulfonyloxy)phenyl]titanium, bis(cyclopentadienyl)bis[2,3,5,6-tetrafluoro-4-(4-tolylsulfonyloxy)phenyl]titanium, bis(cyclopentadienyl)bis[2,3,5,6-tetrafluoro-4-butyryloxy-phenyl]titanium,
bis(cyclopentadienyl)bis[2,6-difluoro-3-(morpholinocarbonyloxy)phenyl]titanium,
bis(cyclopentadienyl)bis[2,6-difluoro-3-(dimethylaminocarbonyloxy)phenyl]titanium,
bis(cyclopentadienyl)bis[2,6-difluoro-3-((butylamino)thiocarbonyloxy)phenyl]titanium,
bis(cyclopentadienyl)bis[2,6-difluoro-3-((phenylamino)thiocarbonyloxy)phenyl]titanium,
bis(cyclopentadienyl)bis[2,6-difluoro-3-(dimethylsulfonyloxy)phenyl]titanium,
bis(cyclopentadienyl)bis[2,6-difluoro-3-(morpholinosulfamyloxy)phenyl]titanium,
bis(cyclopentadienyl)bis[2,6-difluoro-3-(tiimethylsiloxy)phenyl]titanium,
bis(cyclopentadienyl)bis[2,6-difluoro-3-(dimethyl(1,1,2-trimethylpropyl)siloxy)phenyl]titanium,
bis(cyclopentadienyl)bis[2,6-difluoro-3-(dimethylphenylsiloxy)phenyl]titanium,
bis(cyclopentadienyl)bis[2,6-difluoro-3-(tert.-butyldimethylsiloxy)phenyl]titanium,
bis(cyclopentadienyl)bis[2,6-difluoro-3-(cyclohexylcarbonyloxy)phenyl]titanium,
bis(cyclopentadienyl)bis[2,6-difluoro-3-(3-(4-methylcyclohexyl)propanoyloxy)phenyl]titanium,
bis(cyclopentadienyl)bis[2,6-difluoro-3-(3-phenylpropanoyloxy)phenyl]titanium,
bis(cyclopentadienyl)bis[2,6-difluoro-3-((4-methylpiperazino)carbonyloxy)phenyl]titanium,
bis(cyclopentadienyl)bis[2,6-difluoro-3-(6-methoxyadipoyloxy)phenyl]titanium,
bis(cyclopentadienyl)bis[2,6-difluoro-3-((5-ethoxypentan-1,5-dionyl)oxy)phenyl]titanium,
bis(cyclopentadienyl)bis[2,6-difluoro-3-(2-butoxyethanoyloxy)phenyl]titanium,
bis(cyclopentadienyl)bis(2,6-difluoro-4-acetoxyphenyl)titanium,
bis(methylcyclopentadienyl)bis(2,6-difluoro-3-acetoxyphenyl)titanium,
bis(methylcyclopentadienyl)bis[2,6-difluoro-3-(4-tolylsulfonyloxy)phenyl]titanium,
bis(trimethylsilylcyclopentadienyl)bis(2,6-difluoro-3-propionyloxyphenyl)titanium,
bis(pentamethylcyclopentadienyl)bis[2,6-difluoro-3-((butylamino)carbonyloxy)phenyl]titanium,
bis(indenyl)-bis(2,6-difluoro-3-dodecanoyloxyphenyl)-titanium,
bis(4,5,6,7-tetrahydroindenyl)bis(2,6-difluoro-3-acetoxyphenyl)titanium,
bis(cyclopentadienyl)bis(2,6-difluoro-3-methyl-4-propionyloxyphenyl)titanium,
bis(cyclopentadienyl)bis(2,5,6-difluoro-3-acetoxyphenyl)titanium.

The titanocenes of the formula I can be prepared by reacting 1 mole of a compound of the formula V

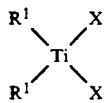  V in which X is halogen, in particular chlorine, with one mole each of the aryllithium compounds LiR² and LiR³. If R² and R³ are identical, 1 mole of V is reacted with 2 moles of LiR². This reaction is carried out analogously to known processes for the preparation of titanocenes from compounds of the formula V, as described, for example, in J. Organomet. Chem. 2 (1964), 206 and 4 (1965), 445, or in EP-A-122,223.

The titanocenes of the formula I are preferably prepared by introducing the —Y—R⁵ radical into the corresponding fluorinated hydroxyaryltitanocenes. This can be achieved by reaction with a) a compound R⁵—Y—X, in which X is halogen, preferably chlorine,
b) a compound (R⁵—CO)₂O, or
c) a compound R⁵—NCO or R⁵—NCS.

The invention therefore also relates to a process for the preparation of compounds of the formula I in which R² and R³ are substituted by a radical of the formula —O—Y—R⁵ by reacting compounds of the formula I in which R² and R³ are substituted by an —OH group with a) either a compound R⁵—Y—X, in which X is halogen, preferably chlorine,
b) with a compound (R 5CO)₂O, or
c) with a compound R⁵NCO or R⁵NCS.

In this case, compounds of the formula I which are preferably reacted are those in which R² and R³ are a group of the formula VI or VII:

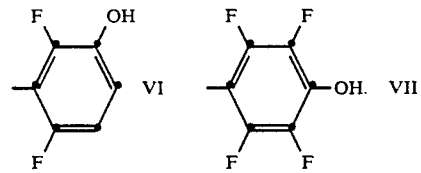

Fluorinated hydroxyphenyltitanocenes of this type, which are used here as intermediates, are novel compounds and are likewise subject-matter of the invention.

They can be prepared by hydrolysis of compounds of the formula I in which R² and R³ are groups of the formula VIII or IX

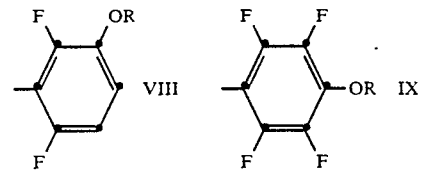

in which R is either a tetrahydropyranyl group or a silyl group of the formula —Si(R⁴)₃, in which R⁴ is as defined above. R⁴ is preferably C₁-C₈alkyl or phenyl, in particular methyl.

The hydrolysis is preferably carried out in an acidic medium.

The reaction of the hydroxyaryltitanocenes with a compound of the formula R⁵—Y—X or (R⁵CO)₂O is preferably carried out with addition of equimolar amounts of a base. This may be, for example, an inorganic base, such as an alkali metal hydroxide or an alkaline earth metal oxide or hydroxide, or an organic amine, such as tributylamine, pyridine or dimethylaniline.

The reaction of the hydroxyaryltitanocenes with a compound R⁵—NCO or R⁵—NCS may be accelerated by adding catalytic amounts of a base. The base used may be, for example, a trialkylamine or a heterocyclic base.

All reactions of the titanocenes are preferably carried out in an inert organic solvent. Examples of suitable solvents for this purpose are benzene, toluene, xylene, tetrahydrofuran, dioxane, 1,2-dichloroethane, dimethylformamide or mixtures of such solvents.

The compounds of the formula I are generally crystalline, usually orange compounds which are distinguished by high thermal stability and only decompose at high temperatures. No decomposition is observed even under the action of air. Many of these compounds can be dissolved, even in relatively high amounts, in curable compositions, and therefore offer valuable applicational properties.

The compounds are stable on storage in the dark and can be handled without a protective gas. They are highly suitable alone as highly effective photoinitiators for the photoinduced polymerization of ethylenically unsaturated compounds. In this case, they are distinguished by very high photosensitivity and effectiveness over a wide wavelength range of from about 200 nm (UV light) to about 600 nm. Furthermore, the titanocenes are also capable of effectively initiating the polymerization under the influence of heat, warming to between 170° C. and 240° C. being expedient. It is of course also possible to use the action of light and warming for the polymerization, warming after irradiation allowing lower temperatures, for example 80°-150° C., for the polymerization.

The present invention furthermore relates to a radiation-polymerizable composition containing (a) at least one non-volatile, monomeric, oligomeric or polymeric compound containing at least one polymerizable ethylenically unsaturated double bond, and (b) at least one titanocene of the formula I as photoinitiator.

The compositions may contain further photoinitiators (c) which are different from (b), for example those of the benzoin alkyl ether, benzophenone, benzil ketal, 4-aroyl-1,3-dioxolane, dialkoxyacetophenone, α-hydroxy- or α-aminoacetophenone, α-hydroxycycloalkyl phenyl ketone type, or mixtures thereof. The advantage is that lower amounts of the titanocenes according to the invention can be used and nevertheless equal or improved photosensitivities can be achieved. The weight ratio of these components (c):(b) can be, for example, from 1:1 to 30:1, preferably 5:1 to 15:1.

The added amount of titanocenes according to the invention depends essentially on economic points of view, their solubilities and on the desired sensitivity. In general, 0.01 to 20, preferably 0.05-1.0 and particularly 0.1 to 5, % by weight are used, relative to the component (a).

Compounds which are suitable as component (a) are ethylenically unsaturated monomeric, oligomeric and polymeric compounds which react by photopolymerization to form high-molecular-weight products, during which they modify their solubility.

Esters of ethylenically unsaturated carboxylic acids and polyols or polyepoxides, and polymers containing ethylenically unsaturated groups in the chain or in side groups, for example unsaturated polyesters, polyamides and polyurethanes, and copolymers thereof, polybutadiene and butadiene copolymers, polyisoprene and isoprene copolymers, polymers and copolymers containing (meth)acrylic groups in the side chains, and mixtures of two or more such polymers, for example, are particularly suitable.

Examples of unsaturated carboxylic acids are acrylic acid, methacrylic acid, crotonic acid, itaconic acid, cinnamic acid, unsaturated fatty acids, such as linolenic acid or oleic acid. Acrylic acid and methyacrylic acid are preferred.

Suitable polyols are aromatic and particularly aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the polyols mentioned, particularly on the aromatic polyols and epichlorohydrin. Furthermore, polymers or copolymers which contain hydroxyl groups in the polymer chain or side groups, for example polyvinyl alcohol and copolymers thereof, or hydroxyalkyl polymethacrylates or copolymers thereof, are also suitable as polyols. Further suitable polyols are oligoesters containing hydroxyl end groups.

Examples of aliphatic and cycloaliphatic polyols are alkylene diols preferably having 2 to 12 C atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of, preferably, 200 to 1500, 1,3-cyclopentanediol, 1,2-, 1,3- or 1,4-cyclohexanediol, 1,4-dihydroxymethylcyclohexane, glycerol, tris($\beta$-hydroxyethyl)amine, trimethylolethane, trimethylolpropane, pentaerythritol, dipentaerythritol and sorbitol.

The polyols may be partially or fully esterified with one or different unsaturated carboxylic acids, it being possible, in partial esters, for the free hydroxyl groups to be modified, for example etherified or esterified with other carboxylic acids.

Examples of esters are: trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol dimethacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol diacrylate and triacrylate, 1,4-cyclobexane diacrylate, bisacrylates and bismethacrylates of polyethylene glycol having molecular weights of 200-1500, or mixtures thereof.

Compounds which are suitable as component (a) are also the amides of identical or different unsaturated carboxylic acids of aromatic, cycloaliphatic and aliphatic polyamines preferably having 2 to 6, particularly 2 to 4, amino groups. Examples of such polyamines are ethylenediamine, 1,2- or 1,3-propylenediamine, 1,2-, 1,3,- or 1,4-butylenediamine, 1,5-pentylenediamine, 1,6-hexylenediarnine, octylenediarnine, dodecylenediamine, 1,4-diaminocyclohexane, isophoronediamine, phenylenediamine, bisphenylenediamine, di-$\beta$-aminoethyl ether, diethylenetriamine, triethylenetetramine, di($\beta$-aminoethoxy)- or di($\beta$-aminopropoxy)ethane. Further suitable polyamines are polymers and copolymers containing amino groups in the side chain and oligoamides containing amino end groups.

Examples of unsaturated amides of this type are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]acrylamide.

Suitable unsaturated polyesters and polyamides are derived, for example, from maleic acid and diols or diamines. Maleic acid may be partially replaced by other dicarboxylic acids. They can be employed together with ethylenically unsaturated comonomers, for example styrene. Polyesters and polyamides may also be derived from dicarboxylic acids and ethylenically unsaturated diols or diamines, particularly from those having relatively long chains with, for example, 6 to 20 C atoms. Examples of polyurethanes are those built up from saturated or unsaturated diisocyanates and unsaturated or saturated diols.

Polybutadiene and polyisoprene and copolymers thereof are known. Examples of suitable comonomers are olefins, such as ethylene, propene, butene, hexane, (meth)acrylates, acrylonitrile, styrene or vinyl chloride. Polymers containing (meth)acrylate groups in the side chain are likewise known. They may be, for example, products of the reaction of epoxy resins based on novolak with (meth)acrylic acid, homopolymers or copolymers of polyvinyl alcohol or hydroxyalkyl derivatives thereof which have been esterified with (meth)acrylic acid, or homopolymers and copolymers of (meth)acrylates which have been esterified with hydroxyalkyl (meth)acrylates.

The photopolymerizable compounds may be employed alone or in any desired mixtures. Mixtures of polyol (meth)acrylates are preferably used.

Benders may also be added to the compositions according to the invention, which is particularly expedient if the photopolymerizable compounds are liquid substances. The amount of binder can be, for example, 5–95, preferably 10–90 and particularly 50–90, % by weight, relative to the total composition. The choice of binder depends on the area of application and properties required for this purpose, such as ability to be developed in aqueous and organic solvent systems, adhesion to substrates and oxygen sensitivity.

Examples of suitable binders are polymers having a molecular weight of from about 5000–2,000,000, preferably 10,000 to 1,000,000. Examples are: homopolymeric and copolymeric acrylates and methacrylates, for example copolymers made from methyl methacrylate/ethyl acrylate/methacrylic acid, poly(alkyl methacrylates), poly(alkyl acrylates); cellulose esters and cellulose ethers, such as cellulose acetate, cellulose acetate butyrate, methylcellulose, ethylcellulose; polyvinylbutyral, polyvinylforrnal, cyclized rubber, polyethers, such as polyethylene oxide, polypropylene oxide, polytetrahydrofuran; polystyrene, polycarbonate, polyurethane, chlorinated polyolefins, polyvinyl chloride, copolymers made from vinyl chloride/vinylidene chloride, copolymers of vinylidene chloride with acrylonitrile, methyl methacrylate and vinyl acetate, polyvinyl acetate, copoly(ethylene/vinyl acetate), polyamides, such as polycaprolactam and poly(hexamethyleneadipamide), polyesters, such as poly(ethylene glycol terephthalate) and poly(hexamethylene glycol succinate).

The compositions according to the invention are suitable as coating agents for substrates of all types, for example wood, paper, ceramics, plastics, such as polyester and cellulose acetate films, and metals, such as copper and aluminium, in which a protecting layer or photographic image is to be applied by photopolymerization. The present invention furthermore relates to the coated substrates and to a process for applying photographic images to the substrates. The coated substrates may also be used as recording material for holograms (volume/phase diagram), in which case it is advantageous that wet development is not necessary for this purpose.

The substrates can be coated by applying a liquid composition, a solution or suspension to the substrate. Liquid compositions without solvents are preferred. It may be expedient here to employ the titanocenes according to the invention in the form of a liquid photoinitiator mixture, containing other photoinitiators, for example a benzil ketal, a 4-aroyl-1,3-dioxolane, a dialkoxyacetophenone, an α-hydroxy- or α-aminoacetophenone, an α-hydroxycycloalkyl phenyl ketone or mixtures thereof. Liquid mixtures comprising liquid to solid photoinitiators and liquid titanocenes or liquid photoinitiators and syrupy to solid titanocenes are particularly advantageous. These mixtures offer applicational advantages and are distinguished by high stability on storage in the dark.

Examples of benzil ketals are those of the formula

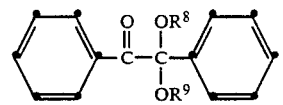

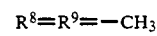

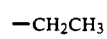

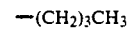

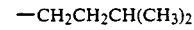

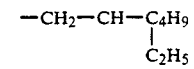

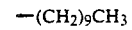

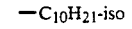

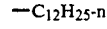

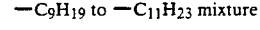

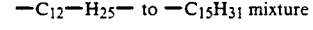

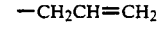

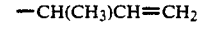

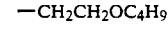

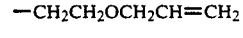

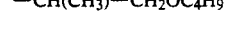

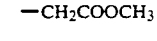

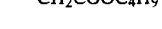

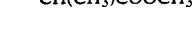

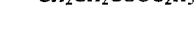

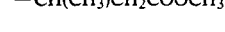

-continued

—CH₂CH₂CH(CH₃)OCH₃

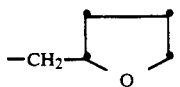

—(CH₂CH₂O)₂CH₃

—(CH₂CH₂O)₂C₂H₅

—(CH₂CH₂O)₂C₄H₉

—(CH₂CH₂O)₃CH₃

—(CH₂CH₂O)₃C₂H₅

—(CH₂CH₂O)₃C₁₂H₂₅

—(CH₂CH₂O)₅C₁₀H₂₁

—(CH₂CH₂O)₈C₉H₁₉ to —C₁₁H₂₃(mixture)

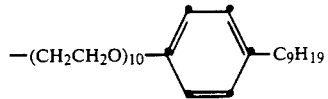

—CH₂CH₂N(C₂H₅)₂

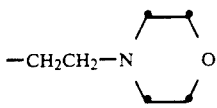

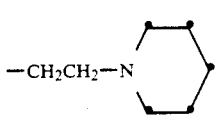

$R^9=CH_3$, $R^8=C_6H_{13}$ $R^9=CH_3$, $R^8=C_{10}H_{21}$ $R^9=CH_3$, $R^8=$ (CH₂CH₂O)₃—C₁₂H₂₅ to —C₁₅H₃₁(mixture)

$R^9=CH_3$, $R^8=$ (CH₂CH₂O)₅—C₉H₁₉ to —C₁₂H₂₃(mixture)

$R^9=CH_3$, $R^8=$ (CH₂CH₂O)₈—C(=O)—C₁₁H₂₃.

Examples of 4-aroyl-1,3-dioxolanes are:
4-benzoyl-2,2,4-trimethyl-1,3-dioxolane
4-benzoyl-4-methyl-2,2-tetramethylene-1,3-dioxolane
cis-trans-4-benzoyl-4-methyl-2,2-pentamethylene-1,3-dioxolane
cis-trans-4-benzoyl-2,4-dimethyl-2-methoxymethyl-1,3-dioxolane
4-benzoyl-4-methyl-2-phenyl-1,3-dioxolane
4-(4-methoxybenzoyl)-2,2,4-trimethyl-1,3-dioxolane
4-(4-methoxybenzoyl)-4-methyl-2,2-pentamethylene-1,3-dioxolane
4-(4-methylbenzoyl)-2,2,4-trimethyl-1,3-dioxolane,
4-benzoyl-2-methyl-4-phenyl-1,3-dioxolane
4-benzoyl-2,2,4,5,5-pentamethyl-1,3-dioxolane
cis-trans-4-benzoyl-2,2,4,5-tetramethyl-1,3-dioxolane,
cis-trans-4-benzoyl-4-methyl-2-pentyl-1,3-dioxolane
cis-trans-4-benzoyl-2-benzyl-2,4-dimethyl-1,3-dioxolane
cis-trans-4-benzoyl-2-(2-furyl)-4-methyl-1,3-dioxolane
4-benzoyl-5-phenyl-2,2,4-trimethyl-1,3-dioxolane
4-(4-methoxybenzoyl)-2,2,4,5,5-pentamethyl-1,3-dioxolane.

Examples of dialkoxyacetophenones are:
α,α-dimethoxyacetophenone
α,α-diethoxyacetophenone
α,α-di-isopropoxyacetophenone
α,α-di-(2-methoxyethoxy)acetophenone
α-butoxy-α-ethoxyacetophenone
α,α-dibutoxy-4-chloroacetophenone
α,α-diethoxy-4-fluoroacetophenone
α,α-dimethoxy-4-methylacetophenone
α,α-diethoxy-4-methylacetophenone
α,α-dimethoxypropiophenone
α,α-diethoxypropiophenone
α,α-diethoxybutyrophenone
α,α-dimethoxyisovalerophenone
α,α-diethoxy-a-cyclohexylacetophenone
α,α-dipropoxy-4-chloropropiophenone.

Examples of α-hydroxy- and α-aminoacetophenones are:
2-hydroxy-2-methyl-1-phenyl-1-propanone
2-hydroxy-2-ethyl-1-phenyl-1-hexanone
1-(4-dodecylphenyl)-2-hydroxy-2-methyl-1-propanone
1-(2,4-dimethylphenyl)-2-hydroxy-2-methyl-1-propanone
2-hydroxy-1-(4-methoxyphenyl)-2-methyl-1-propanone
2-hydroxy-2-methyl-1-phenyl-1-butanone
2-dimethylamino-2-methyl-1-phenyl-1-propanone
2-dibutylamino-2-methyl-1-phenyl-1-propanone
1-(4-fluorophenyl)-2-methyl-2-morpholino-1-pentanone
2-methyl-1-(4-methylthiophenyl)-2-morpholino-1-propanone
2-dimethylamino-1-(4-methoxyphenyl)-2-methyl-1-propanone
2-diethylamino-1-(4-diethylaminophenyl)-2-methyl-1-propanone
2-benzyl-2-dimethylamino-1-(4-methoxyphenyl)-1-butanone
2-benzyl-2-dimethylamino-1-(4-tolyl)-1-butanone
2-benzyl-2-dimethylamino-1-phenyl-1-butanone
2-benzyl-2-dimethylamino-1-(4-chlorophenyl)-1-butanone
2-benzyl-2-dimethylamino-1-(3,4-dimethoxyphenyl)-1-butanone
2-benzyl-2-dimethylamino-1-(3,4-dimethoxyphenyl)-1-pentanone
2-benzyl-2-dimethylamino-1-[4-(2-hydroxyethylthio)-phenyl]-1-butanone
2-dimethylamino-2-(4-methylphenylmethyl)-1-(3,4-dimethoxyphenyl)-1-butanone
2-dimethylamino-2-(4-methylphenylmethyl)-1-(4-morpholinophenyl)-1-butanone
2-benzyl-2-dimethylamino-1-(4-morpholinophenyl)-1-butanone
2-benzyl-2-dimethylamino-1-(4-morpholinophenyl)-1-pentanone
2-benzyl-2-dimethylamino-1-(4-dimethylaminophenyl)-1-butanone
2-allyl-2-dimethylamino-1-(4-morpholinophenyl)-pent-4-en-1-one
2-allyl-1-(4-morpholinophenyl)-2-morpholino-pent-4-en-1-one.

Examples of α-hydroxycycloalkyl phenyl ketones are:
α-hydroxycyclohexyl phenyl ketone
α-hydroxycyclopentyl phenyl ketone The photoinitiator mixture (b)+(c) can be added in amounts of 0.5–20, preferably 1 to 10, by weight, relative to component (a).

The choice of solvent and the concentration depend principally on the nature of the composition and on the coating process. The composition is applied uniformly to a substrate by known coating processes, for example by dipping, knife coating, curtain coating, electrophoresis, brushing, spraying or reverse-roll coating. The amount applied (coating thickness) and the nature of the substrate (coating base) depend on the desired area of application. The coating bases used are: for photographic information recording, for example films made from polyester or cellulose acetate or plastic-coated papers; for offset printing plates, especially treated aluminium, and for the production of printed circuits, copper-laminated laminates. The coating thicknesses for photographic materials and offset printing plates are generally about 0.5 to about 10 μm; for printed circuits, generally 1 to about 100 μm. If solvents are also used, they are removed after coating.

Photocurable compositions as are used for various purposes usually contain a number of other additives in addition to the photopolymerizable compounds and photoinitiators. Thus, it is frequently customary to add thermal inhibitors, which are intended to protect against premature polymerization, particularly during preparation of the compositions by mixing the components. To this end, hydroquinone, hydroquinone derivatives, p-methoxyphenol, β-naphthols or sterically hindered phenols, for example 2,6-di(tert-butyl)-p-cresol, are used for example. Furthermore, small amounts of UV absorbers may be added, for example those of the benzotriazole, benzophenone or oxalanilide type. It is also possible to add light screens of the sterically hindered amine type (HALS).

In order to increase the stability on storage in the dark, copper compounds, such as copper naphthenate, stearate or octanoate, phosphorus compounds, such as triphenylphosphine, tributylphosphine, triethyl phosphite, triphenyl phosphite or tribenzyl phosphite, quaternary ammonium compounds, such as tetramethylammonium chloride or trimethylbenzylammonium chloride, or hydroxylamine derivatives, for example N-diethylhydroxylamine, may be added.

In order to exclude the inhibiting effect of atmospheric oxygen, paraffin or similar waxy substances are frequently added to photocurable mixtures. Due to low solubility in the polymer, these float at the beginning of the polymerization and form a transparent surface layer which prevents ingress of air.

Further customary additives are photosensitizers which absorb in certain wavelengths and pass the absorbed energy to the initiators or themselves function as an additional initiator. Examples of these are, in particular, thioxanthone, anthracene, anthraquinone and coumarine derivatives.

Further customary additives are accelerators of the wine type, which are particularly important in pigmented preparations since they act as chain-transfer agents. Examples of these are N-methyldiethanolamine, triethylamine, ethyl p-dimethylaminobenzoate or Michler's ketone. The action of the amines can be reinforced by adding aromatic ketones of the benzophenone type. Further customary accelerators are 1,3,4-thiadiazole derivatives, for example 2-mercapto-5-methylthio-1,3,4-thiadiazole.

Examples of further customary additives are fillers, pigments, dyes, adhesives, wetting agents and flow-control agents.

Photocuring is extremely important for printing inks, since the drying time of the binder is a crucial factor for the production rate of graphic products and should be in the order of fractions of seconds. UV-curable printing inks are particularly important for screen printing.

The photocurable compositions according to the invention are also highly suitable for the production of printing plates, in particular flexographic printing plates. Here, for example, mixtures of soluble, linear polyamides or of styrene-butadiene rubber with photopolymerizable monomers, for example acrylamides or acrylates, and a photoinitiator are used. Films and plates made from these systems are exposed over the negative (or positive) of the print master, and the non-cured areas are subsequently eluted using a solvent.

A further area of application for photocuring is metal coating, for example in the painting of metal sheeting for tubes, cans or bottle cans, and the photocuring of plastic coatings, for example of PVC-based floor coverings or wall coverings.

Examples of the photocuring of paper coatings are the clear coating of labels, record sleeves or book covers.

The use of the photocurable compositions is also important for imaging processes and for optical production of information carriers. Here, the coating (wet or dry) applied to the backing is irradiated with short-wave light through a photomask, and the unexposed areas of the coating are removed by treatment with a solvent (=developer). The exposed areas are cross-linked and polymeric and are thus insoluble and remain on the backing. When stained appropriately, visible images are produced. If the backing is a metallized layer, the metal can be removed at the unexposed areas by etching after exposure and development or thickened by electroplating. In this way, printed circuits are photoresists can be produced.

The titanocenes according to the invention may also be used as photoinitiators in photocurable compositions for dental applications. They give, with short irradiation times, materials of high strength and low degree of residual unsaturated components. By irradiating dental compositions based on olefinically unsaturated resins, inorganic fillers and titanocene photoinitiators, hardening depths of several millimeters can be achieved within a few seconds using commercial light sources for dental applications. Examples of compositions for dental materials which can be cured using compounds according to the invention, as well as further details on binders, fillers, further additives and application methods, are given, for example, in EP-A-334,338 and DE-A-3,801,511.

Light sources having a high proportion of short-wave light are suitable for the exposure. Today, suitable technical equipment and various types of lamps are available for this purpose. Examples are carbon arc lamps, xenon arc lamps, mercury vapour lamps, metal halogen lamps, fluorescent lamps, argon lamps or photographic floodlamps. Recently, laser light sources have also been used. These have the advantage that photomasks are not necessary; the controlled laser beam writes directly on the photocurable coating.

The examples below illustrate the invention in greater detail.

A) Preparation of hydroxyaryltitanocenes

EXAMPLE 1

Bis(cyclopentadienyl)bis(2,6-difluoro-3-hydroxyphenyl)titanium

1a) 1-Trimethylsiloxy-2,4-difluorobenzene

In a 2.5 l sulfation flask, 260.2 g (2.0 mol) of 2,4-difluorophenol and 242.9 g (2.4 mol) of triethylamine are dissolved in 700 ml of dichloromethane and cooled to 0° C. 239 g (2.2 mol) of trimethylchlorosilane are added dropwise in the course of about 3 hours. The white suspension is allowed to react to completion for 8 hours (check using GC and TLC). The suspension is filtered, the residue is washed with a little dichloromethane, and the filtrate is evaporated on a rotary evaporator. The oil obtained is distilled at 56°–62° C. in vacuo (22 mbar). 280 g of a clear, colourless liquid are obtained.

Analysis: $C_9H_{12}F_2OSi$ (202.28): Calculated: 53.44% C; 5.98% H; 18.79% F; 13.89% Si. Found: 53.3% C; 6.0% H; 18.7% F; 14.1% Si.

1b) Bis(cyclopentadienyl)bis(2,6-difluoro-3-hydroxyphenyl)titanium 18.2 g (0.073 mol) of bis(cyclopentadienyl)titanium dichloride and 34.6 g (0.17 mol) of 1-trimethylsiloxy-2,4-difluorobenzene in 25 ml of absolute tetrahydrofuran are introduced into a sulfation flask under nitrogen as protective gas. The suspension is cooled to −10° C. A solution of lithium diisopropylamide, prepared from 16.2 g (0.16 mol) of diisopropylamine in 25 ml of absolute tetrahydrofuran and 100 ml (0.16 mol) of butyllithium solution in hexane (1.6 molar hexane solution), is then added dropwise over the course of 30 minutes at −10° to 0° C. The mixture is then stirred for a further one hour at 0° C. warmed to room temperature and evaporated on a rotary evaporator in the absence of light (conversion check using GC). The residue is stirred in 100 ml of dichloromethane and filtered through siliceous earth. The filtrate is re-evaporated on a rotary evaporator. The residue is dissolved in 200 ml of dioxane/water mixture (3:1), 18.4 g (0.14 mol) of oxalic acid dihydrate are added, and the mixture is stirred for one hour at room temperature and then diluted with 300 ml of water. The orange suspension is filtered, and the residue is washed with water and dried at 35°–40° C. in vacuo in a drying oven.

24.9 g of an orange powder of melting point 212°–216° C. are obtained.

Analysis: $C_{22}H_{16}F_4O_2Ti$ (436.26): Calculated: 60.57% C; 3.70% H; 17.42% F; 10.98% Ti. Found: 60.50% C; 3.86% H; 17.19F; 10.9% Ti.

EXAMPLE 2

Bis(cyclopentadienyl)bis(2,3,5-tetrafluoro-4-hydroxyphenyl)titanium

2a) 1-Trimethylsiloxy-2,3,5,6-tetrafluorobenzene

In a sulfation flask, 124.6 g (0.75 mol) of 2,3,5,6-tetrafluorophenol are dissolved in 200 ml of absolute acetonitrile. Then, at room temperature and with cooling, first 64.6 g (0.40 mol) of hexamethyldisilazane are added dropwise and subsequently 43.5 g (0.40 mol) of trimethylchlorosilane are slowly added dropwise. The mixture is then stirred for a further two hours at room temperature. The resulting precipitate of ammonium chloride is filtered off and washed with acetonitrile. The combined filters are evaporated on a vacuum rotary evaporator at 20° C. and a pressure of 19 mbar, and the residue is distilled at a pressure of 16 mbar. 140.8 of a colourless oil which boils at 16–18 mbar and a temperature of 63°–64° C. are obtained.

Analysis: $C_9H_{10}F_4OSi$ (238.26): Calculated: 45.37% C; 4.23% H; 31.90% F; 11.79% Si. Found: 45.4% C; 4.2% H; 31.8% F; 11.9% Si.

2b) Bis(cyclopentadienyl)bis(2,3,5,6-tetrafluoro-4-hydroxyphenyl)titanium 600 ml of absolute diethyl ether, 81.0 g (0.80 mol) of diisopropylamine and 6.66 g (0.96 mol) of finely cut lithium wire are introduced at 35° C. into a sulfation flask under nitrogen as protective gas. A mixture of 83.3 g (0.80 mol) of monomeric styrene and 800 ml of absolute diethyl ether is then added dropwise. The temperature is subsequently kept at 35° C. until the lithium metal has dissolved. The mixture is then cooled to −75° C., and a solution of 190.6 g (0.80 mol) of 1-trimethylsiloxy-2,3,5,6-tetrafluorobenzene in 450 ml of absolute cyclohexane is then slowly added dropwise. The mixture is then stirred for a further one hour at −70° C. 99.6 g (0.40 mol) of finely powdered bis(cyclopentadienyl)titanium dichloride are then added. The reaction mixture is protected against light and the temperature is allowed to rise slowly overnight to room temperature. The reaction mixture is then filtered. The residue is washed with diethyl ether. The filtrate is evaporated on a vacuum rotary evaporator with exclusion of light. An orange-red resin is obtained. The crude product is dissolved in 500 ml of methanol, 20 ml of water and 0.1 g of toluene-4-sulfonic acid are added, and the mixture is warmed at 45° C. for two hours. After cooling, an orange-red precipitate deposits overnight, and is filtered off and washed with ethanol. 181 g of product which melts at 174°–178° C. with decomposition are obtained.

EXAMPLE 3

Bis(cyclopentadienyl)bis(2,6-difluoro-3-hydroxyphenyl)titanium

3a) 2-(2,4-Difluorophenoxy)tetrahydro-2H-pyran 260.2 g (2.0 mol) of 2,4-difluorophenol and 252.4 g (3.0 mol) of 3,4-dihydro-2H-pyran are introduced into a 750 ml sulfation flask and cooled to 0° C. One drop of polyphosphoric acid is carefully added to the solution, and the mixture is stirred for a further 16 hours at 0° to 5° C. (check using GC and TLC). The mixture is then reduced alkaline using a little powdered sodium hydroxide. The product is distilled at 119°–120° C. in vacuo (22 mbar). 377 g (88% of theory) of a clear, colourless liquid are obtained.

Analysis: $C_{11}H_{12}F_2O_2$ (214.21): Calculated: 61.68% C; 5.65H. Found: 62.06% C; 6.01% H.

3b) Bis(cyclopentadienyl)bis(2,6-difluoro-3-hydroxyphenyl)titanium 101.2 g (1.0 mol) of diisopropylamine in 300 ml of absolute tetrahydrofuran are introduced into a sulfation flask under nitrogen as protective gas and cooled to −70° C. 625 ml (1.0 mol) of butyllithium solution in hexane (1.6 molar hexane solution) are then added dropwise over the course of about 2 hours, and the mixture is stirred for a further one hour at −70° C. 214.2 g (1.0 mol) of 2-(2,4-difluorophenoxy)tetrahydro-2H-pyran, diluted with 60 ml of absolute tetrahydrofuran, are then added dropwise over the course of one hour. 300 ml of absolute ether and subsequently 113.2 g (0.455 mol) of bis(cyclopentadienyl)titanium dichloride are then added. The mixture is stirred for a further 30 minutes at −70° C. The temperature is then allowed to rise to room temperature over the course of 10 hours. The reaction mixture is evaporated on a rotary evaporator, and the residue is stirred in dichloromethane and filtered through siliceous earth. The filtrate is re-evaporated on a rotary evaporator. The residue is dissolved in 1100 ml of dioxane/water mixture (3:1), 114.6 g (0.91 mol) of oxalic acid dihydrate are added, and the mixture is stirred for one hour at room temperature. The mixture is then diluted with 1000 ml of water. The orange suspension is filtered, and the residue is washed with water and dried at 35°-40° C. in vacuo in a drying oven. 160.1 g of the title compound are obtained as an orange-red powder which melts at 212°-216° C. and is identical with the product of Example 1.

B) Conversions of hydroxyaryltitanocenes

EXAMPLE 4

Bis(cyclopentadienyl)bis(2,6-difluoro-3-acetoxyphenyl)titanium 8.7 g (0.020 mol) of bis(cyclopentadienyl)bis(2,6-difluoro-3-hydroxyphenyl)titanium and 3.8 (0.048 mol) of pyridine in 30 ml of toluene/DMF mixture (1:1) are introduced into a 100 ml sulfation flask under nitrogen as protective gas. 4.9 g (0.048 mol) of acetic anhydride are added dropwise to this solution at room temperature over the course of 5 minutes, and the mixture is stirred for a further 24 hours (reaction check using thin-layer chromatography). The reaction mixture is then poured into ether and water. The ether phase is separated off, washed three times with water, dried using magnesium sulfate and evaporated on a rotary evaporator. The residue is purified by flash chromatography using a hexane/ether mixture 1:1 and, after evaporation, crystallized from an ether/hexane mixture. 7.7 g of a yellow powder of melting point 104°-123° C. (decomposition) are obtained.

Analysis: $C_{26}H_{20}F_4O_4Ti$ (520.34). Calculated: 60.02% C; 3.87% H. Found: 58.97% C; 4.22% H.

EXAMPLE 5

Bis(cyclopentadienyl)bis(2,6-difluoro-3-propionyloxyphenyl)titanium

The compound is prepared analogously to Example 4 using propionic anhydride. The product is obtained as a glassy substance.

Analysis: $C_{28}H_{24}F_4O_4Ti$ (548.39): Calculated: 61.33% C; 4.41% H. Found: 60.72% C; 4.52% H.

EXAMPLE 6

Bis(cyclopentadienyl)bis(2,6-difluoro-3-decanoyloxyphenyl)titanium 6.1 g (0.014 mol) of bis(cyclopentadienyl)bis(2,6-difluoro-3-hydroxyphenyl)titanium and 2.7 g (0.0336 mol) of pyridine in 50 ml of a toluene/DMF mixture (1:1) are introduced into a 100 ml sulfation flask under nitrogen as protective gas. 6.4 g (0.0336 mol) of decanoyl chloride are added dropwise to this red solution at room temperature over the course of 5 minutes, and the mixture is stirred for a further 16 hours (reaction check using thin-layer chromatography). The reaction mixture is then poured into ether and water. The ether phase is evaporated off, washed twice with water, dried using magnesium sulfate and evaporated on a rotary evaporator. The residue is purified by flash chromatography using a hexane/ether mixture 9:1 as eluent, and evaporated on a rotary evaporator. 6.9 g of a red, clear resin are obtained.

Analysis: $C_{42}H_{52}F_4O_4Ti$ (744.77): Calculated: 67.73% C; 7.04% H. Found: 67.74% C; 7.11% H.

EXAMPLE 7

Bis(cyclopentadienyl)bis(2,6-difluoro-3-stearoyloxyphenyl)titanium

The compound is prepared analogously to Example 6 using stearoyl chloride. The product is obtained as an orange-red powder which melts at 77°-78° C.

Analysis: $C_{58}H_{84}F_4O_4Ti$ (969.20): Calculated: 72.03% C; 8.55% H. Found: 71.37% C; 8.72% H.

EXAMPLE 8

Bis(cyclopentadienyl)bis(2,6-difluoro-3-methacryloxyyloxyphenyl)titanium

The compound is prepared analogously to Example 6 using methacryloyl chloride. The product is obtained as an orange-red powder which melts at 226°-228° C.

Analysis: $C_{30}H_{24}F_4O_4Ti$ (572.41): Calculated: 62.94% C; 4.22% H; 13.27% F. Found: 63.20% C; 4.62% H; 12.50% F.

EXAMPLE 9

Bis(cyclopentadienyl)bis[2,6-difluoro-3-(isopropylaminocarbonyloxy)phenyl]titanium 8.7 g (0.020 mol) of bis(cyclopentadienyl)bis(2,6-difluoro-3-hydroxyphenyl)titanium, 4.1 g (0.048 mol) of isopropyl isocyanate and 0.6 g (0.006 mol) of triethylamine (as catalyst) in 50 ml of 1,2-dichloroethane are warmed under reflux (about 83° C.) in a 100 ml sulfation flask under nitrogen as protective gas. After the mixture has been refluxed with stirring for 12 hours, the reaction is complete according to a reaction check using thin-layer chromatography. The reaction mixture is evaporated on a vacuum rotary evaporator and purified by means of flash chromatography using a hexane/ether mixture 1:1 and re-evaporated on the rotary evaporator. 7.0 g of a glassy, orange, powder are obtained.

Analysis: $C_{30}H_{30}F_4N_2O_4Ti$ (606.47): Calculated: 59.41% C; 4.99% H; 4.62% N. Found: 58.6% C; 5.4% H; 4.6% N.

EXAMPLE 10

Bis(cyclopentadienyl)bis[2,6-difluoro-2,6-(butylaminocarbonyloxy)phenyl]titanium The compound is prepared analogously to Example 9 using butyl isocyanate and is obtained as a glassy, orange-red powder.

Analysis: $C_{32}H_{34}F_4N_2O_4Ti$ (634.53): Calculated: 60.57% C; 5.40% H; 4.41% N. Found: 58.64% C; 5.18% H; 3.76% N.

EXAMPLE 11

Bis(cyclopentadienyl)bis[2,6-difluoro-3-(isobutyloxycarbonyloxy)phenyl]titanium 8.7 g (0.020 mol) of bis(cyclopentadienyl)bis(2,6-difluoro-3-hydroxyphenyl)titanium, 3.8 g (0.048 mol) of pyridine and a small spatula tip of 2-dimethylaminopyridine as catalyst are dissolved in 20 ml of dimethylformamide and 30 ml of toluene in a 100 ml sulfation flask under nitrogen. 6.6 g (0.048 mol) of isobutyl chloroformate are added dropwise to this dark-red solution at room temperature over the course of 10 minutes. The reaction mixture is stirred overnight at room temperature until the educt no longer appears in the thin-layer chromatogram. The suspension is poured into 100 ml of ethyl acetate and 100 ml of water, and the mixture is stirred and filtered through Hyflo. The two phases of the filtrate are separated from one another. The organic phase is dried using magnesium sulfate, filtered and evaporated in a vacuum rotary evaporator at 20 mbar and a bath temperature of 40° C. A dark-red oil is obtained and is purified by flash chromatography using hexane/ethyl acetate (3:1) as solvent. 6.6 g (52% of theory) of an orange-red glassy resin are obtained.

Analysis: $C_{32}H_{32}F_4O_6Ti$ (636.49): Calculated: 60.39% C; 5.07% H. Found: 60.1% C; 5.3% H.

EXAMPLE 12

Bis(cyclopentadienyl)bis[2,6-difluoro-3-(4-tolylsulfonyloxy)phenyl]titanium 4.4 g (0.010 mol) of bis(cyclopentadienyl)bis(2,6-difluoro-3-hydroxyphenyl)titanium are suspended in 100 ml of toluene in a sulfation flask under nitrogen as protective gas. 5.7 g (0.030 mol) of toluene-4-sulfonyl chloride are then added. 30 ml of 1N sodiumhydroxide solution (0.030 mol) are then added dropwise. The reaction is slightly exothermic, and the temperature of the reaction mixture gradually increases to 40° C. The mixture is stirred for a further 3 hours while the temperature drops (thin-layer check of the reaction). 100 ml of ice-water and 100 ml of ether are then added. The organic phase is separated off and washed several times with a little water until the washings are neutral. The organic phase is dried using magnesium sulfate and evaporated on a vacuum rotary evaporator. An orange product remains which, after purification by chromatography on silica gel using toluene as eluent, gives orange crystals having a melting point of 185°–187° C.

Analysis: $C_{36}H_{28}F_4O_6S_2Ti$ (744.6): Calculated: 58.07% C; 3.79% H; 10.21% F; 8.61% S. Found: 58.1% C; 3.8% H; 10.3% F; 8.5% S.

EXAMPLE 13

Bis(cyclopentadienyl)bis[2,3,5,6-tetrafluoro-4-(4-tolylsulfonyloxy)phenyl]titanium 5.1 g (0.010 mol) of bis(cyclopentadienyl)bis(2,3,5,6-tetrafluoro-4-hydroxyphenyl)titanium are suspended in 100 ml of toluene in a sulfation flask under nitrogen as protective gas. 5.7 g (0.030 mol) of toluene-4-sulfonyl chloride are then added. 40 ml of 1N sodium hydroxide solution (0.040 mol) are subsequently added dropwise, and the mixture is stirred for 4 hours at 40° C. After a check of the reaction using thin-layer chromatography, the reaction mixture is allowed to cool. 100 ml of ice-water and 100 ml of ether are then added. The organic phase is separated off and washed several times with a little water until the reaction on pH paper is neutral. The organic phase is dried using magnesium sulfate and evaporated on a vacuum rotary evaporator. An orange-red crystalline product remains which, after recrystallization from toluene, melts at 226°–228° C.

Analysis: $C_{36}H_{24}F_8O_6S_2Ti$ (816.60): Calculated: 52.95% C; 2.96% H; 7.85% S; 18.61% F. Found: 53.0% C; 3.0% H; 8.2% S; 18.5% F.

EXAMPLE 14

Bis(cyclopentadienyl)bis[2,6-difluoro-3-(dimethyl-(1,1,2-trimethylpropyl)siloxy)phenyl]titanium 6.1 g (0.014 mol) of bis(cyclopentadienyl)bis(2,6-difluoro-3-hydroxyphenyl)titanium are suspended in 50 ml of toluene in a small flask. The suspension is cooled to between 0° and 5° C., and 1.7 g (0.017 mol) of triethylamine are then added. 3.0 g (0.017 mol) of dimethyl-(1,1,2-trimethylpropyl)chlorosilane are subsequently added dropwise. At first, no reaction occurs. 15 ml of dimethylformamide are then added dropwise until everything has dissolved. The solution is stirred overnight at room temperature. On the next day, the reaction is complete (TLC check). Ether and water are added to the reaction mixture. The organic phase is separated off, washed twice with water and twice with 5% solution hydroxide solution, dried using $Na_2SO_4$, filtered and evaporated on a vacuum rotary evaporator. The red oil is purified by means of flash chromatography using a hexane/ether mixture (1:1). 9.1 g of a yellow-orange resin which slowly crystallizes are obtained. Recrystallization from ethanol gives yellow crystals having a melting point of 112°–115° C.

Analysis: $C_{38}H_{52}R_4O_2Si_2Ti$ (720.90): Calculated: 63.31% C; 7.27% H; 10.54% F. Found: 63.75% C; 7.60% H; 10.03% F.

C) Direct preparation of the substituted titanocenes

EXAMPLE 15

Bis(cyclopentadienyl)bis[2,6-difluoro-3-(trimethylsiloxy)phenyl]titanium 16.2 g (0.16 mol) of diisopropylamine and 25 ml of absolute tetrahydrofuran are introduced into a three-necked flask under nitrogen as protective gas and cooled to 0° C. 100 ml (0.16 mol) of butyllithium solution in hexane (1.6 molar hexane solution) are then added dropwise. The resultant yellow solution of lithium diisopropylamide is subsequently stirred for 10 minutes at 0° C. and then added dropwise over the course of 30 minutes to a suspension of 18.2 g (0.073 mol) of bis(cyclopentadienyl)titanium dichloride and 34.4 g (0.17 mol) of trimethylsiloxy-2,4-difluorobenzene in 25 ml of absolute tetrahydrofuran at −10° to 0° C. The suspension is sniffed for a further one hour at 0° C. The solvent is then removed on a vacuum rotary evaporator. The residue is stirred in 100 ml of dichloromethane and filtered through siliceous earth. The filtrate is re-evaporated on the vacuum rotary evaporator. An orange oil is obtained, which can be crystallized from hexane at −20° C. The melting point is below 20° C.

Analysis: $C_{28}H_{32}F_4O_2Si_2Ti$ (580.62): Calculated: 57.92% C; 5.55 % H. Found: 57.87% C; 5.49% H.

D) Use Examples

EXAMPLE 16

Photocuring of an acrylate mixture

A photocurable composition is prepared by mixing the following components:

|  | Solids content |
|---|---|
| 150.30 g of Scripset 540[1] (30% solution in acetone) | 45.1 g |
| 48.30 g of trimethylolpropane triacrylate | 48.3 g |
| 6.60 g of polyethylene glycol diacrylate | 6.6 g |

|  | Solids content |
|---|---|
| 0.08 g of crystal violet |  |
| 205.28 g | 100.0 g |

[1] Polystyrene-maleic anhydride copolymer (Monsanto)

Portions of this composition are in each case mixed with 0.3% (relative to the solids content) of photoinitiator. All operations are carried out under a red light or yellow light.

The samples mixed with initiator are applied in a thickness of 150 μm to a 200 PM aluminium foil (10×15 cm). The solvent is removed by warming at 60° C. for 15 minutes in a circulation oven. A 76 μm thick polyester film is placed on the liquid coating, and this is covered by a standardized test negative with 21 steps of different optical density (Stouter wedge). This is covered by a second polyester film, and the resultant laminate is fixed onto a metal plate. The sample is exposed with a 5 kill metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 120 seconds using developer A and subsequently dried at 60° for 15 minutes in a circulation oven. The sensitivity of the initiator system used is characterized by indicating the final wedge step imaged without adhesion. The higher the number of steps, the more sensitive the system. An increase by two steps indicates an approximate doubling of the curing rate. The results are given in Table 1. Developer A contains 15 g of sodium metasilicate.9H₂O; 0.16 g of KOH; 3 g of polyethylene glycol 6000; 0.5 g of levulinic acid and 1000 g of deionized water.

TABLE 1

| Titanocene | Number of imaged steps after exposure for | | |
|---|---|---|---|
| Example | 10s | 20s | 40s |
| 6 | 13 | 16 | 19 |
| 7 | 13 | 15 | 18 |
| 8 | 12 | 15 | 17 |
| 9 | 10 | 13 | 15 |
| 11 | 10 | 13 | 17 |
| 12 | 13 | 16 | 18 |
| 13 | 12 | 15 | 18 |

EXAMPLE 17

Photocuring of a monomer/polymer mixture

A photocurable composition is prepared by mixing the following components:

| 37.64 g of | Sartomer SR 444 (pentaerythritol triacrylate) (Sartomer Company, Westchester) |
|---|---|
| 10.76 g of | Cymel 301 (hexamethoxymethylmelamine) (Cyanamid) |
| 47.30 g of | Carboset 525 (thermoplastic polyacrylate containing carboxyl groups/B. F. Goodrich) |
| 4.30 g of | polyvinylpyrrolidone PVP (GAF) |
| 100.00 g of | the above mixture |
| 0.50 g of | Irgalit Green GLN |
| 319.00 g of | methylene chloride |
| 30.00 g of | methanol |
| 450.00 g | |

Portions of this composition are in each case mixed with 0.3% (relative to the solids content) of the titanocenes indicated in the table below. All operations are carried out under a red light or yellow light.

The samples mixed with initiator are applied in a thickness of 200 μm to a 200 μm aluminium foil (10×15 cm). The solvent is removed by warming at 60° C. for 15 minutes in a circulation oven. A 76 μm thick polyester film is placed on the liquid coating, and this is covered by a standardized test negative with 21 steps of different optical density (Stauffer wedge). This is covered by a second polyester film, and the resultant laminate is fixed onto a metal plate. The sample is exposed with a 5 kill metal halide lamp at a distance of 30 cm for 10 seconds for a first test series, for 20 seconds for a second test series and for 40 seconds for a third test series. After the exposure, the films and the mask are removed, the exposed coating is developed in an ultrasound bath for 240 seconds using developer A and subsequently dried at 60° C. for 15 minutes in a circulation oven. The sensitivity of the initiator system used is characterized by indicating the final wedge step imaged without adhesion. The higher the number of steps, the more sensitive the system. An increase by two steps indicates an approximate doubling of the curing rate. The results are given in Table 2.

TABLE 2

| Titanocene | Number of imaged steps after exposure for | | |
|---|---|---|---|
| Example | 10s | 20s | 40s |
| 6 | 13 | 15 | 18 |
| 7 | 13 | 15 | 17 |
| 8 | 11 | 14 | 16 |
| 9 | 11 | 14 | 17 |
| 11 | 11 | 14 | 17 |

What is claimed is:

1. A method for the production of radiation-polymerizable materials including paints, printing inks, printing plates, resist materials, materials for dental applications and image recording materials, which comprises incorporating into or applying to said materials a composition containing
   (a) at least one non-volatile, monomeric, oligomeric or polymeric compound containing at least one polymerizable ethylenically unsaturated double bond, and
   (b) at least one titanocene of the formula I

in which both the $R^1$ radicals, independently of another, are cyclopentadienyl$^\ominus$, indenyl$^\ominus$ or 4,5,6,7-tetrahydroindenyl$^\ominus$, each of which is unsubstituted, monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, —Si($R^4$)$_3$, —Ge($R^4$)$_3$, cyano or halogen, and $R^4$ is $C_1$-$C_{12}$alkyl, $C_5$-$C_8$cycloalkyl, $C_6$-$C_{10}$aryl or $C_7$-$C_{16}$aralkyl, $R^2$ is a 6-membered carbocyclic or 5- or 6-membered heterocyclic aromatic ring which is substituted by fluorine atoms at least in the two ortho-positions to the titanium-carbon bond, and in which the aromatic ring may contain 1 to 2 fluoro atoms as further substituents, and $R^3$, independently, is as defined for $R^2$, $R^2$ and $R^3$ in the titanocenes being substituted by a radical of the formula II $$—O—Y—R^5 \quad\quad II$$

in which Y is a —CO—, —CS—, —CO—O—, —SO$_2$—, Si(R$^4$)$_2$—, —CO—NR$^6$—, —CS—NR$^6$— or —SO$_2$—NR$^6$— group, R$^5$ is linear or branched $C_1$-$C_{20}$alkyl, $C_2$-$C_{20}$alkyl, $C_2$-$C_{20}$alkenyl, $C_3$-$C_8$cycloalkyl, $C_6$-$C_{15}$-cycloalkylalkyl or -alkylcycloalkyl, $C_7$-$C_{16}$-alkylcycloalkylalkyl, $C_6$-$C_{20}$cycloalkenylalkyl, $C_7$-$C_{20}$bicycloalkyl, $C_6$-$C_{14}$aryl, $C_7$-$C_{12}$aralkyl, $C_7$-$C_{20}$alkylaryl or $C_8$-$C_{20}$alkylaralkyl, these radicals being unsubstituted or substituted by $C_1$-$C_{18}$alkoxy, $C_1$-$C_{12}$alkylthio, $C_1$-$C_{18}$alkylsulfonyl, $C_6$-$C_{10}$arylsulfonyl, $C_7$-$C_{20}$alkylarylsulfonyl, —COOH, —CN, —COOR$^4$, —Co—($C_1$-$C_{20}$alkyl) or halogen, R$^6$ is hydrogen or has one of the meanings mentioned for R$^5$, or R$^5$ and R$^6$ together are $C_3$-$C_7$alkylene, which may be interrupted by —O—, —S— or —N(R$^7$)—, in which R$^7$ is hydrogen, $C_1$-$C_{12}$alkyl, $C_3$-$C_{12}$alkenyl, $C_7$-$C_{12}$aralkyl or $C_2$-$C_{20}$alkanoyl.

2. A coated substrate which is coated on at least one surface with a composition containing
   (a) at least one non-volatile, monomeric, oligomeric or polymeric compound containing at least one polymerizable ethylenically unsaturated double bond, and
   (b) at least one titanocene of the formula I

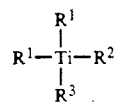

(I)

in which both the R$^1$ radicals, independently of another, are cyclopentadienyl$^\ominus$, indenyl$^\ominus$ or 4,5,6,7-tetrahydroindenyl$^\ominus$, each of which is unsubstituted, monosubstituted or polysubstituted by $C_1$-$C_{18}$alkyl, $C_1$-$C_{18}$alkoxy, $C_2$-$C_{18}$alkenyl, $C_5$-$C_8$cycloalkyl, $C_6$-$C_{10}$aryl, $C_7$-$C_{16}$aralkyl, —Si(R$^4$)$_3$, —Ge(R$^4$)$_3$, cyano or halogen, and R$^4$ is $C_1$-$C_{12}$alkyl, $C_5$-$C_8$cycloalkyl, $C_6$-$C_{10}$aryl or $C_7$-$C_{16}$aralkyl, R$^2$ is a 6-membered carbocyclic or 5- or 6-membered heterocyclic aromatic ring which is substituted by fluorine atoms at least in the two ortho-positions to the titanium-carbon bond, and in which the aromatic ring may contain 1 or 2 fluoro atoms as further substituents, and R$^3$, independently, is as defined for R$^2$, R$^2$ and R$^3$ in the titanocenes being substituted by a radical of the formula II $$—O—Y—R^5 \quad\quad II$$

in which I is a —CO—, —CS—, —CO—O—, —SO$_2$—, —Si(R$^4$)$_2$, —CO—NR$^6$—, —CS—NR$^6$— or —SO$_2$—NR$^6$— group, R$^5$ is linear or branched $C_1$-$C_{20}$alkyl, $C_2$-$C_{20}$alkyl, $C_2$-$C_{20}$alkenyl, $C_3$-$C_8$cycloalkyl, $C_6$-$C_{15}$cycloalkylalkyl or -alkylcycloalkyl, $C_7$-$C_{16}$-alkylcycloalkylalkyl, $C_6$-$C_{20}$cycloalkenylalkyl, $C_7$-$C_{20}$bicycloalkyl, $C_6$-$C_{14}$aryl, $C_7$-$C_{12}$aralkyl, $C_7$-$C_{20}$alkylaryl or $C_8$-$C_{20}$alkylaralkyl, these radicals being unsubstituted or substituted by $C_1$-$C_{18}$alkoxy, $C_1$-$C_{12}$alkylthio, $C_1$-$C_{18}$alkylsulfonyl, $C_6$-$C_{10}$arylsulfonyl, $C_7$-$C_{20}$alkylarylsulfonyl, —COOH, —CN, —COOR$^4$, —CO—($C_1$-$C_{20}$alkyl) or halogen, R$^6$ is hydrogen or has one of the meanings mentioned for R$^5$, or R$^5$ and R$^6$ together are $C_3$-$C_7$alkylene, which may be interrupted by —O—, —S—, or —N(R$^7$)—, in which R$^7$ is hydrogen, $C_1$-$C_{12}$alkyl, $C_3$-$C_{12}$alkenyl, $C_7$-$C_{12}$aralkyl or $C_2$-$C_{20}$alkanoyl.

3. A process for the photographic production of relief images, wherein a coated substrate according to claim 2 is exposed imagewise, and the unexposed areas are then removed using a solvent.

4. A method for photopolymerisation of non-volatile, monomeric, oligomeric or polymeric compounds, containing at least one polymerizable, ethylenically unsaturated double-bond, which comprises adding to said compounds a titanocene of the formula I according to claim 2, alone or together with other photoinitiators, and irradiating with light in the range from 200 to 600 nm.

* * * * *